US009969761B2

(12) United States Patent
Wickstrom et al.

(10) Patent No.: US 9,969,761 B2
(45) **Date of Patent: *May 15, 2018**

(54) STABILISATION OF RADIOPHARMACEUTICAL PRECURSORS

(71) Applicants: GE HEALTHCARE LIMITED, Buckinghamshire (GB); GE HEALTHCARE AS, Oslo (NO)

(72) Inventors: Torild Wickstrom, Oslo (NO); Dirk-Jan In't Veld, Oslo (NO); Nigel John Osborn, Amersham (GB); Julian Grigg, Amersham (GB); Anthony Wilson, Waddesdon (GB)

(73) Assignees: GE HEALTHCARE AS, Oslo (NO); GE HEALTHCARE LIMITED, Buckinghamshire (GB)

(*) Notice: Subject to any disclaimer, the term of this patent is extended or adjusted under 35 U.S.C. 154(b) by 72 days.

This patent is subject to a terminal disclaimer.

(21) Appl. No.: 14/258,247

(22) Filed: Apr. 22, 2014

(65) Prior Publication Data

US 2015/0018541 A1 Jan. 15, 2015

Related U.S. Application Data

(63) Continuation of application No. 11/721,563, filed as application No. PCT/GB2005/004448 on Nov. 18, 2005.

(30) Foreign Application Priority Data

Dec. 22, 2004 (GB) .................................. 0428020.2

(51) Int. Cl.
*C07H 13/04* (2006.01)
*C07H 1/00* (2006.01)

(52) U.S. Cl.
CPC .............. *C07H 13/04* (2013.01); *C07H 1/00* (2013.01)

(58) Field of Classification Search
None
See application file for complete search history.

(56) References Cited

U.S. PATENT DOCUMENTS 4,794,178 A 12/1988 Coenen et al.
5,759,513 A 6/1998 Nakazawa
5,932,178 A 8/1999 Yamazaki et al.
6,015,895 A 1/2000 Pon et al.
6,545,134 B1 4/2003 Eschenmoser et al.

FOREIGN PATENT DOCUMENTS

EP 0588480 3/1994
FR 2863876 6/2005
FR 2864898 7/2005
JP 63303911 12/1988
WO 94/21643 9/1994
WO WO1994021653 A1 9/1994
WO 2004/052357 6/2004
WO 2004/069285 8/2004
WO 2005/000210 1/2005
WO WO2005000210 A2 1/2005
WO WO 2006/067366 A1 * 6/2006

OTHER PUBLICATIONS

Nishijima, K. et al., Applied Radiation and Isotopes, "Increased [18F]2-fluoro-2-deoxy-D-glucose ([18F]FDG) yield with recycled target [18O]water: factors affecting the [18F]FDG yield", 2002, vol. 57, pp. 43-49.*

"Derivative", Merriam-Webster OnLine Dictionary; also available at http://www.merriam-webster.com/dictionary/derivative; last viewed Jul. 15, 2009.*

Hunt, Ian, Organic Chemistry etext, Chapter 25: Carbohydrates, "Mutarotation", University of Calgary; also available at http://www.chem.ucalgary.ca/courses/351/Carey5th/Ch25/ch25-3-3.html; last viewed Jun. 22, 2017.*

Yuasa, et.al. Applied Radiation Isotope vol. 48, No. 2, pp. 201-305.

Aldridge Catalog, 1998-1999, Sigma-Aldrich, 1998 p. 12.

thefreedictionary.com, "storage", also available at http://www.thefreedictionary.com/p/storage; last viewed Sep. 8, 2011.

Merriam-Webster OnLine Dictionary "derivative"; also available at http://www.merriam-webster.com/dictionary/derivative; last viewed Jul. 15, 2009.

ABX advanced biochemical compounds, Mannose Triflate, ultra pure Data Sheet, published Dec. 20, 2004; also available at http://www.abx.de/chemicals/100.html, or via the Internet Archive Waybackmachine http://web.archive.org/web/20041220180627/http://www.abx.de/chemicals/100.html.

Hamacher, K. et al., Appl. Radiat. Isot., "Computer-aided Synthesis (CAS) of No-carrier-added 2-[18F]Fluoro-2-deoxy-D-glucose: an Efficient Automated System for the Aminopolyether-supported Nucleophilic Fluorination", 1990, vol. 41, pp. 49-55.

GB0428020.2 Search Report dated Apr. 2005.

PCT/GB2005/004448 Int'l Search Report and Written Opinion dated Apr. 2006.

Patent Abstracts of Japan vol. 013, No. 137 Apr. 1989.

Abstract from Advanced Biochemical Compounds www.abx.de Mannose Triflate, ultra pure Product No. 100, 101, 102 and 105.

Chirakal, et.al., "Base-mediated decomposition of a mannose triflate during the synthesis of 2-Deoxy-2-18F-fluoro-D-glucose" Appl. Radiat. Osot. vol. 46, No. 3, pp. 149-155 1995.

(Continued)

*Primary Examiner* — Layla D Berry
*Assistant Examiner* — Bahar Craigo
(74) *Attorney, Agent, or Firm* — Wood IP LLC

(57) ABSTRACT

The present invention relates to a method for improving stability of non fluoridated sugar derivatives, and in particular glucose derivatives such as 1,3,4,6-tetra-O-acetyl-2-O-trifluoromethanesulfonyl-β-D-mannopyranose which are used as precursors for production of radiofluoridated sugar derivatives for use in in vivo imaging procedures such as positron emission tomography (PET). The method comprises storing the non fluoridated sugar derivative in an organic solvent. The resultant formulations of the non fluoridated sugar derivative and cassettes for automated synthesis apparatus comprising the same are also claimed.

7 Claims, 4 Drawing Sheets

(56) References Cited

OTHER PUBLICATIONS

Figure 1:
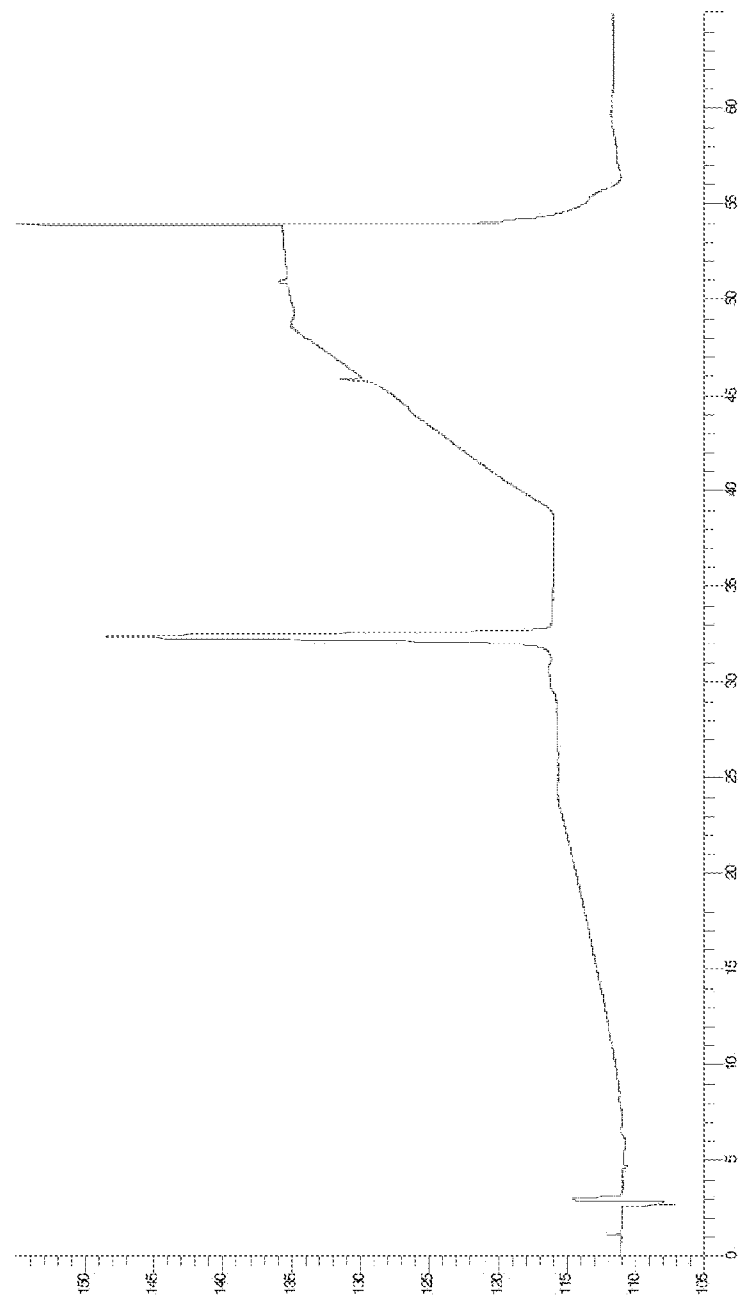

Search Report dated Apr. 27, 2016 in corresponding Brazil Application No. P10519582-9 filed Nov. 18, 2005. (English Translation enclosed).

Ken-ichi Nishijima et al., "Increased [18F]2-fluoro-2-deoxy-D-glucose ([18F]FDG) yield with recycled target [18O]water: factors affecting the [18F]FDG yield," Applied Radiation and Isotopes, vol. 57, pp. 43-49, 2002.

* cited by examiner

STABILISATION OF RADIOPHARMACEUTICAL PRECURSORS

This application is a continuation of pending U.S. application Ser. No. 11/721,563, filed Jun. 4, 2009, which in turn is a filing under 35 U.S.C. 371 of international application number PCT/GB2005/004448, filed Nov. 18, 2005, which claims priority to application number 0428020.2 filed Dec. 22, 2004, in Great Britain the entire disclosure of which is hereby incorporated by reference.

The present invention relates to a method for improving stability of non fluoridated sugar derivatives, and in particular glucose derivatives which are used as precursors for production of radiofluoridated sugar derivatives for use in in vivo imaging procedures such as positron emission tomography (PET). The invention further includes formulations of non fluoridated sugar derivatives, and cassettes for automated synthesis apparatus comprising the same.

Non fluoridated sugar derivatives such as 1,3,4,6-tetra-O-acetyl-2-O-trifluoromethanesulfonyl-β-D-mannopyranose (commonly known as mannose triflate) are currently supplied commercially as dry powders and need to be stored at sub-ambient temperatures to ensure stability over a reasonable period, the shelf life of dry powder mannose triflate is 6 months at 5° C. In the context of an automated radiofluoridation system such as TracerLab MX (Coincidence Technologies), this means that the mannose triflate has to be stored separately from the other reagents and assembled into the cassette by the operator prior to running the radiofluoridation process. Therefore, there exists the need for a method to improve stability of non fluoridated sugar derivatives such as mannose triflate to improve shelf-life and preferably allow storage at ambient temperature, for example, in the same package as the other reagents or as part of a preassembled cassette.

The present inventors have surprisingly found that by storing a non fluoridated sugar derivative, such as mannose triflate in an organic solvent rather than as a dry powder, the stability is improved. This runs contrary to expectations as normally degradation would be expected to occur more quickly in solution. Presentation of a non fluoridated sugar derivative, such as mannose triflate in an organic solvent has the further advantage that, being already in solution, dissolution of the non fluoridated sugar derivative, such as mannose triflate prior to performing radiofluoridation can be avoided which may be particularly advantageous in an automated radiochemistry operation.

Therefore, according to one aspect of the invention, there is provided a method for improving stability of a non fluoridated sugar derivative which comprises storage of said non fluoridated sugar derivative in a solvent in a sealed container.

The solvent used in the method may be an aprotic solvent (as defined more fully below) or a protic solvent. Suitable protic solvents include $C_{1-8}$alcohols, for example methanol, ethanol, isopropanol, isobutanol, acetone or octanol. The solvent used may be dry, meaning having a water content of 10000 ppm or less, suitably 1000 ppm or less, more suitably less than 600 ppm, and preferably less than 100 ppm.

In one aspect of the invention, it is advantageous that the non fluoridated sugar derivative is stored in the same solvent which will be used subsequently in the fluoridation reaction. This avoids an extra step of solvent removal before fluoridation. Therefore, according to a further aspect of the invention, there is provided a method for improving stability of a non fluoridated sugar derivative which comprises storage of said non fluoridated sugar derivative in an aprotic solvent in a sealed container.

Suitable aprotic solvents for this purpose include acetonitrile, dimethylformamide, dimethylsulfoxide, tetrahydrofuran, dioxan, 1,2-dimethoxyethane, sulfolane and N-methylpyrrolidinone. However, acetonitrile has been found to be a particularly suitable solvent for storage. The aprotic solvent used may be dry, meaning having a water content of 1000 ppm or less, suitably less than 600 ppm, and preferably less than 100 ppm. In an alternative embodiment of the invention, the aprotic solvent used may have a water content of between 1000 ppm and 50000 ppm, suitably a water content of 1000 ppm to 15000 ppm, more suitably 1500 ppm to 7000 ppm or 1800 ppm to 7000 ppm, and more suitably 1500 ppm to 7000 ppm or 1800 ppm to 2500 ppm. Using an aprotic solvent with such a controlled water content has the added advantage that the non fluoridated sugar derivative may be presented in solution having the optimum water content for performing a subsequent radiofluoridation reaction, thus avoiding the need to adjust the water content, for example by a drying step or by addition of further water or solvent.

As used herein, the term "ppm", when describing water content of a given solvent, means μgram water/gram.

Suitably, the non fluoridated sugar derivative is present in the solvent, suitably an aprotic solvent at a concentration suited for performing a subsequent radiofluoridation reaction, for example from 0.1 mg/ml to 50 mg/ml, more suitably 5 mg/ml to 25 mg/ml, even more suitably 10 mg/ml to 18 mg/ml. In one particular embodiment, the non fluoridated sugar derivative is present in the solvent, suitably an aprotic solvent at a concentration of 15 mg/ml. In a further embodiment, the non fluoridated sugar derivative is present in the solvent, suitably an aprotic solvent at a concentration of 17.5 to 21.5 mg/ml.

Suitable sealed containers are those which do not interact with the solvent or with the non fluoridated sugar derivative, optionally permit maintenance of sterile integrity, plus optionally an inert headspace gas (e.g. nitrogen or argon), whilst also optionally permitting addition and withdrawal of solutions by syringe. Such containers include liquid-tight or gas-tight jars, flasks, ampoules and vials, the seal being provided by a liquid-tight or gas-tight closure such as a lid, stopper, or septum. A preferred such container is a septum-sealed vial, wherein the gas-tight closure is crimped on with an overseal (typically of aluminium). Such containers have the additional advantage that the closure can withstand vacuum if desired for example to change the headspace gas or degas solutions and can withstand an overpressure, for example to aid in the removal of the solution from the container.

Using the methods described herein, the non fluoridated sugar derivative may be stored for extended periods of 2 days or more, for example up to 18 months, suitably up to 6 months, more suitably for up to 8 weeks, at temperatures at or below ambient, for example at −10° C. to 35° C., suitably 10° C. to 35° C. As mentioned above, storage at ambient temperature is particularly convenient.

In the alternative, there is provided a formulation of a non fluoridated sugar derivative comprising said non fluoridated sugar derivative, and a solvent in a sealed container as described hereinbefore. The solvent present in the formulation may be an aprotic solvent or a protic solvent as described above.

In the alternative, there is further provided a formulation of a non fluoridated sugar derivative comprising said non fluoridated sugar derivative, and an aprotic solvent in a sealed container as described hereinbefore.

In the present specification, the term "non fluoridated sugar derivative" refers to a polysaccharide, oligosaccharide, disaccharide or monosaccharide sugar in which one of the OH groups is replaced by a leaving group and the other OH groups of the sugar are each optionally protected with a suitable protecting group. Such non fluoridated sugar derivatives are suitably derivatives of monosaccharides such as glucose, fructose, ribose, arabinose, mannose or galactose, most suitably glucose derivatives. Particular non fluoridated sugar derivatives used in the invention are those of formula (I):

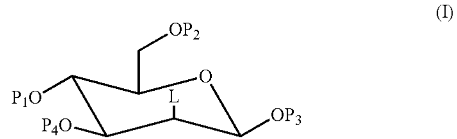

wherein L is a leaving group and $P_1$ to $P_4$ are each a suitable protecting group.

Suitable protecting groups which may be present in the non fluoridated sugar derivatives used in the invention are well known in the art and are described, for example, in "Protecting Groups in Organic Synthesis", Theodora W. Greene and Peter G. M. Wuts, published by John Wiley & Sons Inc. The particular protecting group chosen will depend upon the intended process for preparation of the fluoridated product but, for example, the hydroxy groups may be protected by conversion to alkyl or aromatic esters, for example by reaction with an alkanoyl chloride such as acetyl chloride. Alternatively, hydroxy groups may be converted to ethers, for example alkyl or benzyl ethers. Preferably, the protecting groups $P_1$ to $P_4$ are each an acyl group.

Suitable leaving groups are also well known in the art and include arylsulphonates such as toluene sulfonate, haloalkylsulphonates, and alkylsulphonates such as methane sulfonate. It is particularly preferred, however, that the leaving group is a trifluoromethane sulfonate (triflate) group.

A particularly preferred non fluoridated sugar derivative is 1,3,4,6-tetra-O-acetyl-2-O-trifluoromethanesulfonyl-β-D-mannopyranose, commonly referred to as "mannose triflate". Mannose triflate is a commercially available non fluoridated sugar derivative which is used as a precursor for synthesis of 2-[$^{18}$F]fluoro-D-glucose ([$^{18}$F]FDG) via the protected intermediate 2-fluoro-1,3,4,6-tetra-O-acetyl-D-glucose (tetraacetylfluorodeoxyglucose or pFDG).

As would be apparent to a person skilled in the art, a formulation according to the invention may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid). And such ingredients may be added as part of a method according to the invention. However, presence of such ingredients is avoided where possible so that the radiofluoridated sugar derivative may be produced in as pure a form as possible for subsequent use in an in vivo imaging procedure. Therefore, formulations and methods as described herein in which the non fluoridated sugar derivative and solvent are present in the sealed container without further ingredients.

Radiotracers, such as [$^{18}$F]FDG are now often prepared on an automated radiosynthesis apparatus using nucleophilic radiofluoridation chemistry with $^{18}F^-$, based on the reagent Kryptofix™ 2.2.2. There are several examples of such apparatus commercially available, including Tracerlab MX (Coincidence Technologies SA) and Tracerlab FX (Nuclear Interface GmbH). Such apparatus commonly comprises a cassette, often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

A formulation of a non fluoridated sugar derivative as described herein may be housed in a disposable or removable cassette designed for use with the automated synthesis apparatus. Therefore, the invention further provides a cassette for an automated synthesis apparatus comprising a formulation of a non fluoridated sugar derivative comprising said non fluoridated sugar derivative, and a solvent in a sealed container as described hereinbefore. As demonstrated herein, the improved stability of the non fluoridated sugar derivative when stored as a formulation according to the invention means that the cassette can be provided complete with all of the reagents required for the fluoridation reaction, except for the radiofluoride, and the cassette can be stored at ambient temperature thus avoiding the need for refrigeration.

The invention is illustrated by way of the examples below, in which the following abbreviations are used:

MT or mannose triflate: 1,3,4,6-tetra-O-acetyl-2-O-trifluoromethanesulfonyl-β-D-mannopyranose.

HPLC: high performance liquid chromatography

IR: infrared spectrometry

UV: ultraviolet

RCP: radiochemical purity pFDG: 2-fluoro-1,3,4,6-tetra-O-acetyl-D-glucose

EXAMPLE 1: STABILITY OF MANNOSE TRIFLATE IN DRY ACETONITRILE

With reference to the Figures:

FIG. 1: HPLC-UV chromatogram of Mannose Triflate from ABX (solid material) at start.

Figure 2:
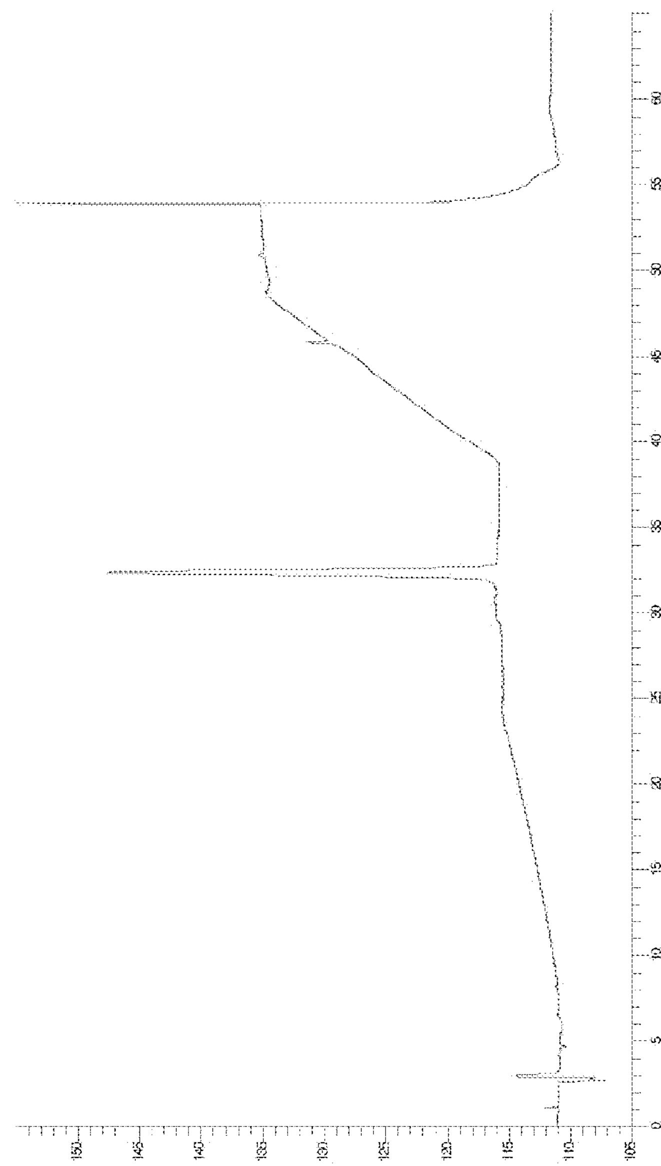

FIG. 2: HPLC-UV chromatogram of Mannose Triflate from ABX (dissolved in acetonitrile) at start.

Figure 3:
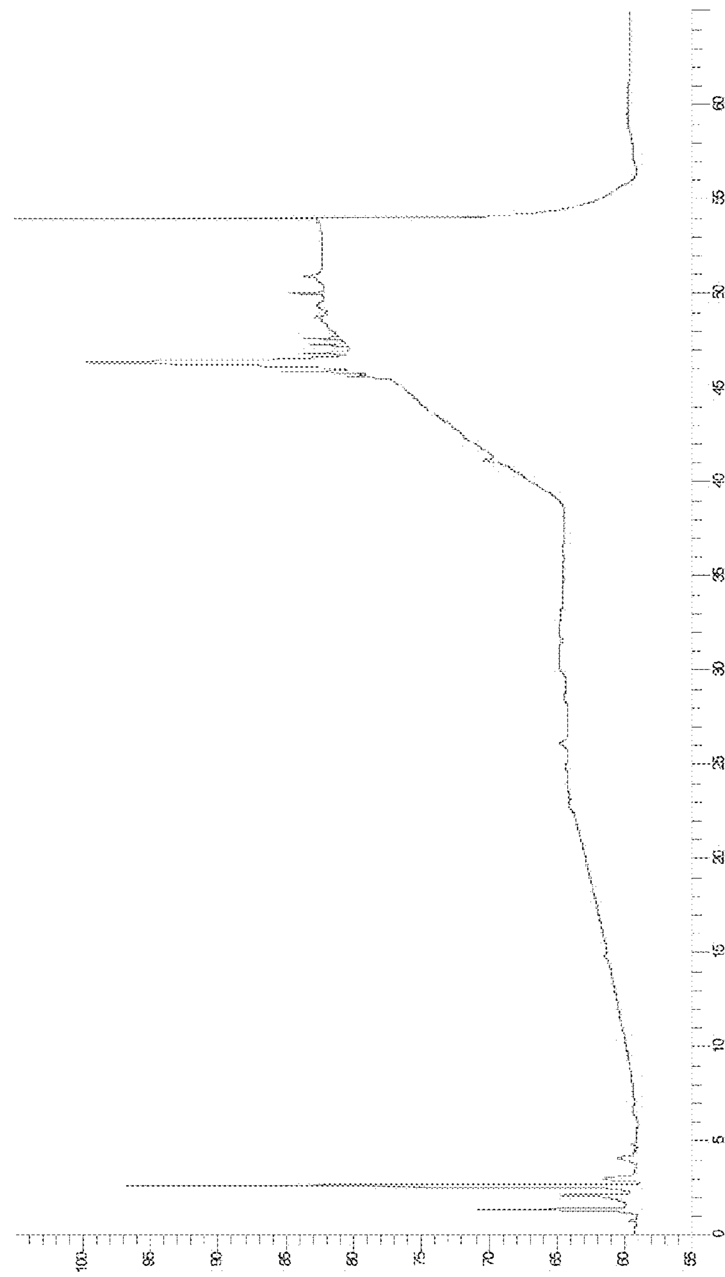

FIG. 3: HPLC-UV chromatogram of Mannose Triflate from ABX (solid material) stored for 2 weeks at 50° C.

Figure 4:
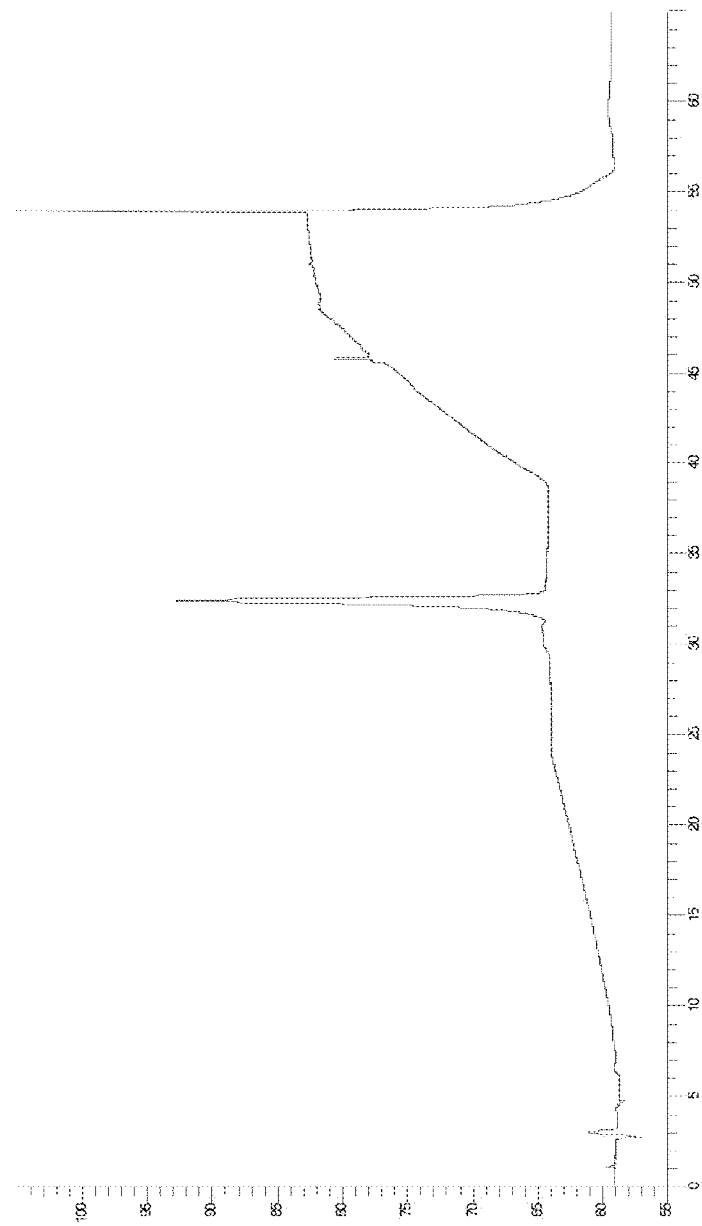

FIG. 4: HPLC-UV chromatogram of Mannose Triflate from ABX (dissolved in acetonitrile) stored for 2 weeks at 50° C.

Materials:

Acetonitrile (MeCN): VWR/Merck, 4 L, water content approximately 600 ppm.

Mannose triflate ABX: Ultra-pure quality 1 g units,

Vials: Fiolax 5 ml Glass vials (13 mm), Munnerstaedter.

Stoppers: West 4432/50 gray 13 mm, Teflon coated.

Caps: Helvoet Pharma

Experimental

Glass vials to be used are dried before use in a Lytzen heat sterilizer at 210° C. for 5 hours. Stoppers are not treated in any way.

2.0 g Mannose triflate was weighed into an Erlenmeyer flask and dissolved in 133 ml dry acetonitrile to yield an acetonitrile solution in an extraction hood. Dissolution was rapid, solid disappeared as soon as it came in contact with the acetonitrile.

Dispensing:

This solution was dispensed using a 10 ml glass volumetric cylinder into vial samples of approx. 4.2-4.4 ml.

Control samples of mannose triflate (without solvent) under air and under nitrogen were also prepared.

Filled and capped units are kept in storage at 25° C. and 50° C. in thermally controlled cabinets for set periods of time at which "pull points" a vial was removed from storage and subjected to the testing outlined below.

Test Methods Used:

Non-radioactive methods (cold) performed:

Appearance/organoleptic test, all pull points

Purity by HPLC-UV, all pull points $^{19}$F-NMR, all pull points

Water content analysis, at time zero.

HPLC Method: octadecylsilyl silica gel (5 μm) column (Hichrom Nucleosil 100-5C18), temperature 25° C.; injection volume 20 μl; mobile phase of water: acetonitrile gradient, 1 ml/min. Detection by spectrophotometer at 220 nm.

Radioactive methods (hot) performed: Radiolabelling with $^{18}F^{-}$ in a glassy carbon reactor (all pull points). Each dry sample of mannose triflate (20 mg) is dissolved in dry acetonitrile (1.6 ml). For the mannose triflate stored in acetonitrile, an aliquot (3.3 ml) was removed and diluted to 4.0 ml with acetonitrile and 1.6 ml of this solution was used in the radiolabelling test. For the samples taken after 2 weeks storage at 50° C., a 1.6 ml sample of the mannose triflate solution was used directly without further dilution. In all cases, the radiolabelling was performed after drying an $^{18}$F solution of Kryptofix 2.2.2 (19.4 mg), potassium carbonate (41.0 mg), acetonitrile (0.32 ml) and water (0.04 ml) for 4 minutes at 80° C. before adding the test solution of mannose triflate in acetonitrile. The labelling reaction was carried out at 80° C. for 4 minutes in a glassy carbon reactor.

Results:

HPLC-UV traces for the solid mannose triflate control experiment and the acetonitrile solution of mannose triflate are shown in FIGS. 1 and 2 respectively. Mannose triflate elutes at 32.5 minutes.

After 2 weeks storage at 50° C., all samples of mannose triflate stored as dry powder were black and smelled strongly of acetic acid. No radiolabelling was attempted, IR showed that the material was no longer mannose triflate. The HPLC-UV trace is shown in FIG. 3, no mannose triflate was detected.

After 2 and 4 weeks storage at 50° C., the solutions in acetonitrile however, were still colourless and looked unchanged. Results from HPLC-UV showed one peak indicating no degradation of MT (FIG. 4).

Results from radiolabelling in the glassy carbon reactor at time zero and after storage for different periods at 50° C. are shown in table 1.

TABLE 1

| Sample | Storage Time (weeks) | MT (mg) | Acetonitrile (ml) | pFDG RCP % |
|---|---|---|---|---|
| Control (air) | 0 | 20 | 1.6 | 87 |
| Control (air) | 0 | 20 | 1.6 | 86 |
| Control ($N_2$) | 0 | 20 | 1.6 | 82 |
| Control ($N_2$) | 0 | 20 | 1.6 | 93 |
| MT/acetonitrile (15 mg/ml) | 0 | 20 | 1.6 | 91 |
| MT/acetonitrile (15 mg/ml) | 0 | 20 | 1.6 | 92 |
| MT/acetonitrile (15 mg/ml) | 2 | 24 | 1.6 | 86 |
| MT/acetonitrile (15 mg/ml) | 2 | 24 | 1.6 | 85 |
| MT/acetonitrile (15 mg/ml) | 3 | 20 | 1.6 | 65 |
| MT/acetonitrile (15 mg/ml) | 3 | 20 | 1.6 | 90 |
| MT/acetonitrile (15 mg/ml) | 4 | 20 | 1.6 | 88 |
| MT/acetonitrile (15 mg/ml) | 4 | 20 | 1.6 | 90 |
| MT/acetonitrile (15 mg/ml) | 8 | 20 | 1.6 | 76 |
| MT/acetonitrile (15 mg/ml) | 8 | 20 | 1.6 | 95 |

Conclusion:

The combination of good labelling and good chemical stability by HPLC even after 8 weeks at 50° C. leads to the conclusion that a clear stabilisation has been achieved by dissolving MT in acetonitrile.

EXAMPLE 2: STABILITY OF MANNOSE TRIFLATE IN ACETONITRILE/WATER

Using similar method to Example 1, the stability of mannose triflate in acetonitrile with water at level of approximately 725, 1450, and 2500 ppm was evaluated.

Results from radiolabelling in the glassy carbon reactor at time zero and after storage for different periods at 50° C. are shown in table 2.

TABLE 2

| Sample | Water Content of MT solution (ppm) | Storage Time (weeks) | MT (mg) | Acetonitrile/ water (ml) | pFDG RCP % |
|---|---|---|---|---|---|
| MT/acetonitrile (15 mg/ml) | 2435 | 0 | 20 | 1.6 | 90 |
| MT/acetonitrile (15 mg/ml) | 2435 | 0 | 20 | 1.6 | 78 |
| MT/acetonitrile (15 mg/ml) | 1402 | 0 | 20 | 1.6 | 93 |
| MT/acetonitrile (15 mg/ml) | 725 | 0 | 20 | 1.6 | 89 |
| MT/acetonitrile (15 mg/ml) | 725 | 0 | 20 | 1.6 | 92 |
| MT/acetonitrile (15 mg/ml) | 2499 | 2 | 20 | 1.6 | 91 |
| MT/acetonitrile (15 mg/ml) | 2499 | 2 | 20 | 1.6 | 76 |
| MT/acetonitrile (15 mg/ml) | 1450 | 2 | 20 | 1.6 | 94 |
| MT/acetonitrile (15 mg/ml) | 1450 | 2 | 20 | 1.6 | 91 |
| MT/acetonitrile (15 mg/ml) | 2524 | 4 | 20 | 1.6 | 96 |
| MT/acetonitrile (15 mg/ml) | 2524 | 4 | 20 | 1.6 | 87 |
| MT/acetonitrile (15 mg/ml) | 1470 | 4 | 20 | 1.6 | 87 |
| MT/acetonitrile (15 mg/ml) | 1470 | 4 | 20 | 1.6 | 87 |

COMPARATIVE EXAMPLE: STABILITY OF DRY POWDER MANNOSE TRIFLATE

Dry powder mannose triflate was stored in vials at different temperatures and for different time periods.

Radiolabelling Method

A solution of potassium carbonate (41 mg of potassium carbonate in 40 μl water) was added to a glassy carbon reactor and then a solution of kryptofix 222 (19.4 mg in 320 μl) was added separately. Then a solution of 18-fluoride in water (0.05 ml) was added and the solution dried by heating to 80° C. for 4 mins with a flow of dry nitrogen (at 0.3 liters/min). A solution of 1,3,4,6-tetra-O-acetyl-2-O-trifluoromethanesulfonyl-β-D-mannopyranose (20 mg in 1.6 ml dry acetonitrile) was then added and the reaction heated for a further 4 minutes at 80° C. The reaction was then cooled to 50° C. and a sample removed for analysis by ITLC (Instant thin layer chromatography) on TLC aluminium sheets silica gel 60 F254 eluting with 95% acetonitrile, 5% water. The radiochemical purity was calculated from the ratio of 1,3,4,6-tetra-O-acetyl-2-fluoro-β-D-mannopyranose to the total of the sugar and free fluoride (the sole two components from the reaction). Results of the radiolabelling are shown in Table 3.

TABLE 3

| Storage Conditions and time | % RCP |
|---|---|
| 0 days under air | 87 |
| 0 days under air | 86 |
| 1 day @ room temperature under dry $N_2$ | 82 |
| 1 day @ room temperature under dry $N_2$ | 93 |
| 127 days @ 25° C. under air | 1 |
| 5 days @ 50° C. under air. | 5 |

The data support significant instability of the mannose triflate at room temperature which is much worse when heated to 50° C. The mannose triflate soon becomes black at elevated temperatures and becomes increasingly difficult to dissolve in acetonitrile.

What is claimed is:

1. A formulation of 1,3,4,6-tetra-O-acetyl-2-O-trifluoromethanesulfonyl-β-D-manno pyranose consisting of 1,3,4,6-tetra-O-acetyl-2-O-trifluoromethanesulfonyl-β-D-manno pyranose in acetonitrile forming a solution that is stored in a sealed container, wherein the acetonitrile has a water content of between 100 ppm and 50000 ppm.

2. The formulation of claim 1, wherein the sealed container is a septum-sealed vial.

3. The formulation of claim 1, wherein the solution has a concentration of 10 mg/mL to 18 mg/mL.

4. The formulation of claim 1, wherein the acetonitrile has a water content in a range of about 1000 ppm to about 50000 ppm.

5. The formulation of claim 1, wherein the acetonitrile has a water content of 100 ppm to 600 ppm.

6. The formulation of claim 1, wherein the acetonitrile has a water content of 100 ppm to 1000 ppm.

7. A cassette for an automated synthesis apparatus comprising a formulation according to claim 1.

* * * * *

UNITED STATES PATENT AND TRADEMARK OFFICE

CERTIFICATE OF CORRECTION

PATENT NO. : 9,969,761 B2
APPLICATION NO. : 14/258247
DATED : May 15, 2018
INVENTOR(S) : Wickstrom et al.

It is certified that error appears in the above-identified patent and that said Letters Patent is hereby corrected as shown below:

On the Title Page

Item (72) Inventor:
First Inventor should read: Lill Torild WICKSTROM

Signed and Sealed this
Third Day of September, 2019

Andrei Iancu
*Director of the United States Patent and Trademark Office*